United States Patent [19]

Freedman

[11] Patent Number: 5,149,714
[45] Date of Patent: Sep. 22, 1992

[54] ANTIDEPRESSANTS

[75] Inventor: Jules Freedman, Cincinnati, Ohio

[73] Assignee: Merrell Dow Pharmaceuticals Inc., Cincinnati, Ohio

[21] Appl. No.: 569,259

[22] Filed: Aug. 15, 1990

Related U.S. Application Data

[60] Continuation of Ser. No. 434,665, Nov. 13, 1989, abandoned, which is a continuation-in-part of Ser. No. 401,518, Aug. 29, 1989, abandoned, which is a continuation of Ser. No. 296,474, Jan. 12, 1989, abandoned, which is a division of Ser. No. 287,517, Dec. 19, 1988, abandoned, which is a continuation of Ser. No. 85,665, Aug. 14, 1987, abandoned.

[51] Int. Cl.$^5$ ............... A61K 31/135; C07C 211/03
[52] U.S. Cl. ................... 514/655; 514/653; 514/654; 544/174; 544/378; 546/206; 548/576; 564/355; 564/360; 564/387
[58] Field of Search ............ 564/387, 355, 360; 514/655, 653, 654

[56] References Cited

U.S. PATENT DOCUMENTS

| | | | |
|---|---|---|---|
| 3,883,537 | 5/1975 | Schroder | 564/387 X |
| 3,890,330 | 6/1975 | Werner | 564/378 |
| 4,062,840 | 12/1977 | van der Burg | 564/387 X |
| 4,177,292 | 12/1979 | Nedelec et al. | 564/428 X |
| 4,254,056 | 3/1981 | Konno et al. | 564/387 |
| 4,314,081 | 2/1982 | Molloy et al. | 564/347 |
| 4,755,534 | 7/1988 | Stuetz | 564/387 X |

FOREIGN PATENT DOCUMENTS

| | | |
|---|---|---|
| 0207600 | 1/1987 | European Pat. Off. |
| 1067659 | 5/1967 | United Kingdom |
| 2091250 | 7/1982 | United Kingdom |

OTHER PUBLICATIONS

Wolff, "Burger's Medicinal Chemistry", Part III, 4th Ed., pp. 1014–1015 and 1047 (1979).

E. Mutschler in "Arzneimittelwirkungen", 5th ed., 1986.
Helwig & Helwig, "Moderne Arzneimittel", 5th ed. 1980.

Primary Examiner—Glennon H. Hollrah
Assistant Examiner—Brian M. Burn
Attorney, Agent, or Firm—Louis J. Wille

[57] ABSTRACT

The present invention provides novel aryloxy indanamines of the formula

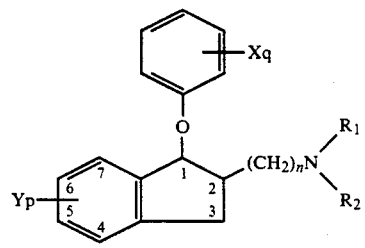

wherein n, p and q are each independently 0, 1 or 2, Y and X are each independently lower alkyl, lower alkoxy, hydroxy, $CF_3$, halogeno or when p or q are 2 and each of the Y or each of the X groups are on adjacent aryl carbon atoms, both of the X or both of the Y groups can be taken together to form a methylenedioxy moiety, $R_1$ and $R_2$ are each independently hydrogen, lower alkyl, aralkyl, or $R_1$ and $R_2$ taken together with the nitrogen to which they are attached are pyrrolidino, morpholino, piperidino, piperazino, or 4-methylpiperazino, or an acid addition salt thereof, which are useful as antidepressants and as inhibitors of synaptic norepinephrine and serotonin uptake.

18 Claims, No Drawings

ANTIDEPRESSANTS

CROSS-REFERENCE TO RELATED APPLICATION

This a continuation of application Ser. No. 434,665, filed Nov. 13, 1989, now abandoned, which is a continuation-in-part of Ser. No. 401,518, filed Aug. 29, 1989, now abandoned, which is a continuation of application Ser. No. 296,474, filed Jan. 12, 1989, now abandoned, which is a divisional of application Ser. No. 287,517, filed Dec. 19, 1988, now abandoned, which is a continuation of application Ser. No. 085,665, filed Aug. 14, 1987, now abandoned.

The present invention provides novel aryloxyindanamines of the formula (1)

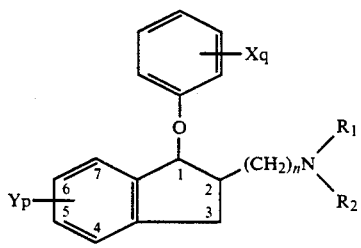

wherein p and q are each independently 0, 1 or 2, n is 1

Y and X are each independently lower alkyl, lower alkoxy, hydroxy, $CF_3$, halogeno or qhen p or q are 2 and each of the Y or each of the X groups are on adjacent aryl carbon atoms, both of the X or both of the Y groups can be taken together to form a methylenedioxy moiety, $R_1$ and $R_2$ are each independently hydrogen, lower alkyl, aralkyl, or $R_1$ and $R_2$ taken together with the nitrogen to which they are attached are pyrrolidino, morpholino, piperidino, piperazino, or 4-methylpiperazino, or an acid addition salt thereof.

The aryloxy moiety of compounds of formula (1) can be mono- or di-substituted at any feasible position(s) in the ring (when q is 1 or 2, respectively) or it can be unsubstituted (when q is 0). X is independently chosen each time it is taken so that when q is 2 the aryloxy moiety is di-substituted with the same or different substituents. Likewise, the fused-ring moiety can be mono- or di-substituted at any of the 4, 5, 6, or 7 position(s) (when p is 1 or 2, respectively) or it can be unsubstituted (when p is 0). Y is independently chosen each time it is taken so that when p is 2 the fused-ring moiety is di-substituted with the same or different substituents. $R_1$ and $R_2$ can be independent moieties or they can be taken together with the nitrogen to which they are attached to form a pyrrolidino, morpholino, piperidino, piperazino, or 4-methylpiperazino group.

As used herein, the term "lower alkyl" refers to an alkyl group comprised of 1 to 6 carbon atoms in straight, branched, or cyclic configuration. The term "lower alkoxy" refers to a lower alkyl group substituted with a single oxygen atom which is attached to the appropriate aryl carbon. The term "halogeno" refers to a fluoro, chloro, bromo or iodo substituent. The term "methylenedioxy" refers to a $-O-CH_2-O-$ moiety attached to adjacent aryl carbon atoms. The term "aralkyl" refers to an aromatic ring attached to the nitrogen atom by a $C_1$ to $C_4$ alkylene bridge. For example, the term "aralkyl" includes, but is not limited to benzyl, and the like.

Compounds wherein $R_1$ and/or $R_2$ are $CO_2Me$ or $CO_2Et$, i.e., the methyl or ethyl ester of a carboxy group, are novel intermediates useful in the preparation of compounds of the formula (1). These esters can be made by utilizing procedures analogous to those described below for compounds of the formula (1) and by utilizing standard procedures well known and appreciated in the art.

Compounds of the formula (1) can be employed as free amines or as acid addition salts thereof. The term "acid addition salts" encompasses both organic and inorganic acid addition salts including, for example, those prepared from acids such as hydrochloric, oxalic, and the like. For example, compounds of the formula (1) wherein X or Y is $CF_3$ can be converted to the hydrochloric acid addition salt using conventional methods well known in the art.

As will be recognized and appreciated by those skilled in the art, the compounds of formula (1) can exist in a form wherein the aryloxy moiety and the amino moiety are in a CIS or TRANS isomeric configuration. It is understood that the present invention encompasses both the CIS and TRANS forms individually and mixtures thereof. Furthermore, it will be recognized and appreciated by those skilled in the art that the CIS and TRANS forms of the compounds of formula (1) possess chiral centers and therefore both the CIS and the TRANS forms can exist in a $(+)$ or a $(-)$ stereoisomeric configuration. It is understood that the present invention encompasses both the $(+)$ and the $(-)$ forms individually and mixtures thereof.

In general, the compounds of formula (1) may be prepared by chemical reactions analogously known in the art, the choice of any specific route of preparation being dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (1). In preparing these compounds, standard procedures and techniques which are well known and appreciated by those of ordinary skill in the art are utilized.

For example, compounds of the formula (1) can conveniently be made according to the general synthetic route outlined in Scheme A.

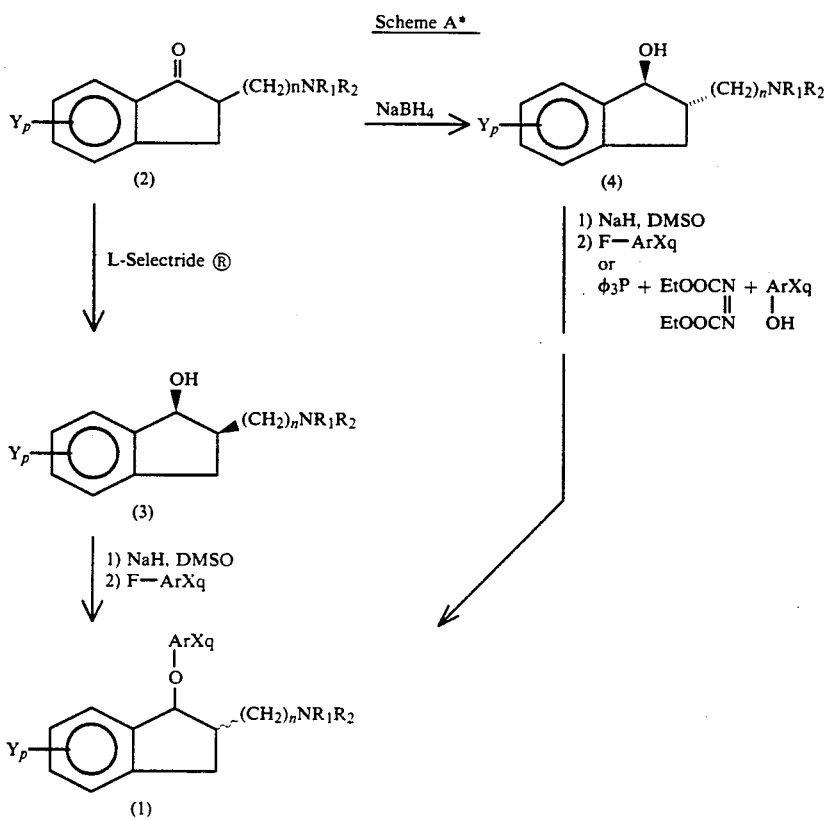

*The Yp, Xq, R1, R2, substituents are as previously defined.

In general, compounds of the formula (1) can be prepared by reacting the appropriately substituted amino ketone (2) with L-Selectride ® (lithium tri-O-isobutyl borohydride available form Aldrich Chemical Co.) to give the amino alcohol (3). This generally results in the CIS isomer in substantially pure form. The sodium derivative of the amino alcohol (3) which is formed by reacting (3) with sodium hydride (NaH) in dimethylsulfoxide (DMSO) is further reacted with the appropriately substituted aryl fluoride (F-ArXq) in the presence of DMSO to give the corresponding compound of the formula (1). Again this generally results in the CIS isomer in substantially pure form or in a mixture of the CIS and TRANS isomers.

Alternatively, compounds of the formula (1) can be prepared by reacting the appropriately substituted amino ketone (2) with sodium borohydride (NaBH$_4$) which gives the amino alcohol (4) in substantially pure TRANS isomeric form. The compounds of the formula (1) can then be formed by reacting the sodium derivative of the amino alcohol (4) with the appropriately substituted aryl fluoride as described above. In the alternative, the amino alcohol (4) can be reacted with the appropriately substituted aryl alcohol (HO—ArX) in the presence of triphenyl phosphine ($\phi_3$P) and diethylazodicarboxylate (EtOOCN=NCOOEt). This procedure can yield compounds of the formula (1) in substantially pure CIS or TRANS forms or in a mixture thereof.

Where compounds of formula (1) are desired wherein R$_1$ or R$_2$ are hydrogen, appropriately substituted amino ketones (2) are selected so as to provide aryloxyindanamine derivatives which can then be de-alkylated or de-blocked by standard procedures and techniques as are well known and appreciated in the art. For example, where a compound of formula (1) is desired wherein one of R$_1$ and R$_2$ is alkyl and the other is hydrogen, an amino ketone derivative (2), wherein R$_1$ is the desired alkyl and R$_2$ is methyl or benzyl, can be utilized to prepare the the corresponding di-substituted aryloxyindanamine (1), which can then be de-methylated or de-benzylated according to standard techniques. For example the N-alkyl-N-methyl- or the N-alkyl-N-benzyl-substituted aryloxyindanamine derivative can be converted to the corresponding carbamate derivative by reaction with a chloroformate ester such as phenylchloroformate. The carbamate derivative can then be hydrolyzed with base such as sodium hydroxide to yield the desired compound of formula (1).

Where it is desired to resolve and isolate the CIS or TRANS isomeric forms of a compound of the formula (1) from a mixture thereof, this resolution can be effected by standard procedures and techniques as are well known and appreciated in the art. For example, the CIS and TRANS forms can be separated by chromatographic techniques.

The stereoisomeric (+) and (−) forms of each of the CIS and TRANS isomers of the compounds of the present invention can be resolved by procedures and techniques as are well known and appreciated in the art. For example, for compounds of formula (1) wherein one of R$_1$ and R$_2$ is hydrogen, the diastereomeric amides of R-α-methoxyphenylacetic acid can be prepared. These diastereomeric amides can then be resolved using column chromatography. The resolved (+) and (−) isomers can then be hyrolyzed back to the amine in pure form.

The following examples serve to illustrate synthetic procedures utilized to make compounds of the formula (1) according to the procedure outlined in Scheme A. These examples are intended to be illustrative only and are not intended to limit the invention in any way. The following terms are defined as indicated: grams (g), degrees Celsius (°C.), moles (M), milliliters (ml), melting point (mp), boiling point (bp).

EXAMPLE 1

CIS-2,3-dihydro-1-(2-methoxyphenoxy)-N,N-dimethyl-1H-indene-2-methanamine

STEP A;
CIS-2,3-Dihydro-2-(N,N-dimethylaminomethyl)-inden-1-ol

To an ice-cooled suspension of 2.25 g (0.01M) of 2,3-dihydro-2-(N,N-dimethylaminomethyl)-1H-inden-1-one hydrochloride in 50 ml of dry tetrahydrofuran add 25 ml of a 1M solution of L-Selectride ®. Stir the mixture for 1.5 hours and decompose with 5 ml of 10% sodium hydroxide solution. Evaporate the solvent at reduced pressure and distribute the residue between ether and water. Separate the ether layer and extract with dilute hydrochloric acid. Basify the acid extract to yield an oil. Extract the oil into ethyl acetate. Evaporate the solvent and Kugelrohr distill at 90°–100°/0.4 mm to yield 0.92 g (48% yield) of the title compound.

Anal. Calcd for $C_{12}H_{17}NO$: C=75.35; H=8.96,; N=7.32. Fd: C=74.86; H=9.00; N=7.25.

By procedures analogous to that described above, the following amino alcohols can be prepared:

CIS-2,3-dihydro-2-(N-methyl-N-phenylmethylamino)methyl-1H-inden-1-ol
bp 135°–140°/0.3 mm
Anal. Calcd for $C_{18}H_{21}NO$: C=80.86; H-7.92; N-5.24. Fd: C=80.68; H=7.95; N=5.21.

CIS-6-chloro-2,3-dihydro-2-(N,N-dimethylamino)methyl-1H-inden-1-ol
bp 118°–121°/0.3 mm
Anal. Calcd for $C_{12}H_{16}ClNO$: C=63.85; H=7.15; N=6.21. Fd: C=63.80; H=7.30; N=6.31.

CIS-2,3-dihydro-2-(4-morpholino)methyl-1H-inden-1-ol
bp 119°–127°/0.3 mm
Anal. Calcd. for $C_{14}H_{19}NO_2$: C=72.07; H=8.21; N=6.00. Fd: C=71.81; H=8.15; N=5.77.

CIS-2,3-dihydro-6-methoxy-2-dimethylaminomethylinden-1-ol
bp 102°–110°/0.3 m
Anal. Calcd for $C_{13}H_{15}NO_2$: C=70.55; H-8.66; N=6.33. Fd: C=70.23; H=8.86; N=6.20.

CIS-2,3-dihydro-6-fluoro-2-dimethylaminomethylinden-1-ol
bp 90°–93°/0.3 m
Anal Calcd. for $C_{12}H_{16}FNO$: C=68.87; H=7.71; N=6.60. Fd: C=68.82; H=7.82; N=6.52.

CIS-2,3-dihydro-5-fluoro-2-(N,N-diethylamino)methyl-1H-inden-1-ol

CIS-2,3-dihydro-3,3-dimethyl-2-(N,N-dimethylamino)methyl-6-methoxy-1H-inden-1-ol CIS-2,3-dihydro-2-(N-ethyl-N-methylamino)methyl-5,6-dimethoxy-1H-inden-1-ol CIS-2,3-dihydro-6-fluoro-2-(4-methylpiperazino)methyl-1H-inden-1-ol CIS-2,3-dihydro-2-(1-pyrolidino)-1H-inden-1-ol CIS-2,3-dihydro-2-(N,N-dimethylamino)ethyl-1H-inden-1-ol STEP B:
CIS-2,3-dihydro-1-(2-methoxyphenoxy)-N,N-dimethyl-1H-indene-2-methanamine Heat a mixture of 0.75 g of 50% sodium hydride dispersion in oil and 10 ml of dimethylsulfoxide in an oil bath at 65° in a nitrogen atmosphere for 30 minutes and then cool to room temperature. Add CIS-2,3-dihydro-2-(N,N-dimethylaminomethyl)-inden-1-ol (1.91 g, 0.01 M) and stir the mixture for 15 minutes. Add 2-fluoroanisole (3.5 ml) and heat the mixture at 90° overnight. After cooling and diluting with water, extract the product into ethyl acetate. Isolate the amine by chromatography on silica, eluting with 10% ethyl acetate in hexane. Kugelrohr distill the eluant at 123°–125°/0.4 mm to yield the title compound.

Anal. Calcd. for $C_{19}H_{23}NO_2$: C=76.73; H=7.80; N=4.71. Fd: C=76.62; H=7.99; N=4.98.

By procedures analogous to that described above, the following compounds of the formula (1) can be prepared:

CIS-2,3-dihydro-N-methyl-N-(phenylmethyl)-1-(4-trifluoromethylphenoxy)-1H-indene-2-methanamine hydrochloride
mp 218°
Anal. Calcd. for $C_{25}H_{24}F_3NO \cdot HCl$: C=67.03; H=5.63; N=3.13. Fd C=67.16; H=5.57; N=3.16.

CIS-2,3-dihydro-N,N-dimethyl-1phenoxy-1H-indene-2-methanamine
bp 110°–115°/0.3 mm
Anal. Calcd for $C_{18}H_{21}NO$: C=80.86; H=7.92; N=5.24. Fd: C=80.58; H=7.93; N=5.01.

CIS-2,3-dihydro-N,N-dimethyl-1-(4-trifluoromethylphenoxy)-1H-indene-2-methanamine hydrochloride
mp 178°–180°
Anal. Calcd for $C_{19}H_{20}F_3NO \cdot HCl$: C=61.37; H=5.69; N=3.77. Fd: C=61.23; H=5.79; N=3.70.

CIS 4-{[2,3-dihydro-1-(2-methoxyphenoxy)-1H-inden-2-yl]methyl}morpholine oxalate
mp 144°–145°
Anal. Calcd. for $C_{21}H_{25}NOhd 3 \cdot C_2H_2O_4$: C=64.32; H=6.34; N-3.26. Fd: C=64.08; H=6.47; N=3.19.

CIS-1-(3,4-dichlorophenoxy)-2,3-dihydro-N,N-dimethyl-1H-indene-2-methanamine hydrochloride
mp 192°–193°
Anal. Calcd for $C_{18}H_{19}Cl_2NO \cdot HCl$: C=58.00; H=5.41; N-3.76. Fd: C=58.11; H=5.49; N=3.68.

CIS-6-chloro-2,3-dihydro-1-(2-methoxyphenoxy)-N,N-dimethyl-1H-indene-2-methanamine maleate
mp 141°–143°
Anal. Calcd. for $C_{19}H_{22}ClNO_2 \cdot C_4H_4O_4$: C=61.67; H=5.85; N=3.13. Fd: C=61.39; H=5.97; N=3.01.

CIS-2,3-dihydro-N,N-dimethyl-1-(2-methylphenoxy)-1H-indene-2-methanamine oxalate CIS-2,3-dihydro-N,N-dimethyl-1-phenoxy-1H-indene-2-amine CIS-2,3-dihydro-1-(3,4-dimethoxyphenoxy)-N,N-dimethyl-1H-indene-2-methanamine CIS-1-(3-chlorophenoxy)-2,3-dihydro-3,3,N,N-tetramethyl-6-methoxy-1H-indene-2-methanamine

EXAMPLE 2

CIS and TRANS-2,3-dihydro-1-phenoxy-N,N-dimethyl-1H-inden-2-amine

Step A:
TRANS-2,3-dihydro-2-dimethylaminomethyl-inden-1-ol

To an ice-cooled solution of 15 g of sodium borohydride in 500 ml of water, add dropwise a solution of 44 g (0.19 M) of 2,3-dihydro-2-N,N-dimethylaminomethyl-inden-1-one hydrochloride in 500 ml of water. Stir the solution at room temperature for 3 hours and extract with chloroform. Evaporate the solvent to yield an oil. Crystallize the oil from heptane to yield 32 g of the title compound.

TRANS-2,3-dihydro-2-dimethylaminomethyl-inden-1-ol
mp 65°–67°
Anal. Calcd. for $C_{12}H_{17}NO$: C=75.35; H=8.96; N=7.32. Fd: C=75.32; N=8.96; N=7.26.

By procedures analogous to that described above, the following amino alcohols can be prepared:

TRANS-2,3-dihydro-6-fluoro-2-dimethylaminomethylinden-1-ol
mp 93°–95°
Anal. Calcd. for $C_{12}H_{16}FNO$: C=68.87; H=7.71; N=6.69. Fd: C=69.02; H=7.84; N=6.57.

Step B: CIS and TRANS-2,3-dihydro-1-phenoxy-N,N-dimethyl-1H-inden-2-amine

Stir a solution of TRANS-2,3-dihydro-2-dimethylamino methyl-inden-1-ol (7.65 g, 0.04 M) triphenylphosphine (11.54 g, 0.044 M), and phenol (4.14 g, 0.044 M) in 100 ml of tetrahydrofuran. Slowly add a solution of diethyl azodicarboxylate in 50 ml of tetrahydrofuran dropwise. Stir the mixture overnight and evaporate the solvent. Take up the residue in ether, filter insoluble material and reconcentrate. Chromatograph the residue on silica gel eluting with ether to yield two isomers, CIS and TRANS, with the CIS isomer eluting first.

Distill the crude CIS isomer to yield 3.0 g of the CIS isomer of the title compound, bp=120°–25° C. at 0.4 mm Hg.
Anal. Calcd. for $C_{18}H_{21}NO$ (CIS): C=80.66; H=7.92; N=5.24. Fd: C=80.67; H=7.95; N=5.17.

Distill the crude TRANS isomer to yield 1.1 g of the TRANS isomer of the title compound, bp=110°–15° C. at 0.3 mm Hg.
Anal. Calcd for $C_{18}H_{21}NO$ (TRANS): C=80.66; H=7.92; N=5.24. Fd: C=80.58; H=7.93; N=5.01.

EXAMPLE 3

CIS-2,3-dihydro-N-methyl-1-[4-trifluoromethyl)-phenoxy]-1H-inden-2-methanamine hydrochloride STEP A;
CIS-2,3-Dihydro-2-(N-benzyl-N-methyl-aminomethyl)-inden-1-ol To an ice-cooled suspension of 3.46 g (0.01M) of 2,3-dihydro-2-(N-benzyl-N-methyl-aminomethyl)-1H-inden-1-one hydrobromide in 50 ml of dry tetrahydrofuran add 25 ml of a 1M solution of L-Selectride ®. Stir the mixture for 1.5 hours and decompose with 5 ml of 10% sodium hydroxide solution. Evaporate the solvent at reduced pressure and distribute the residue between ether and water. Separate the ether layer and extract with dilute hydrochloric acid. Basify the acid extract to yield an oil. Extract the oil into ethyl acetate. Evaporate the solvent and Kugelrohr distill at 90°–100°/0.4 mm to yield 1.78 g (67%) of the title compound [bp=135°–40° C. at 0.3 mmHg].
Anal. Calcd for $C_{18}H_{21}NO$: C=80.49; H=7.98; N=5.41. Fd: C=80.68; H=7.95; N=5.21.

STEP B:
CIS-2,3-dihydro-1-(4-trifluoromethylphenoxy)-N-benzyl-N-methyl-1H-indene-2-methanamine hydrochloride Heat a mixture of 0.75 g of 50% sodium hydride dispersion in oil and 10 ml of dimethylsulfoxide in an oil bath at 65° C. in a nitrogen atmosphere for 30 minutes and then cool to room temperature. Add CIS-2,3-dihydro-2-(N-benzyl-N-methyl-aminomethyl)-inden-1-ol (2.67 g, 0.01 M) and stir the mixture for 30 minutes at 55° C. Add 4-fluorobenzotrifluoride (2.0 ml) and heat the mixture at 90° overnight. After cooling and diluting with water, extract the product into ethyl acetate. Isolate the amine by chromatography on silica and elute with 10% ethyl acetate in hexane. Kugelrohr distill at 123°–125°/0.4 mm to give the pure amine. Convert the pure amine to the hydrochloride by treatment with ethereal hydrogen chloride to yield the title compound [melting point=218° C. (dec.)].
Anal. Calcd. for $C_{25}H_{24}F_3NO.HCl$: C=67.03; H=5.63; N=3.13. Fd: C=67.16; H=5.57; N=3.16.

Step C: Phenyl N [CIS-2,3-dihydro-1-(4-trifluoromethyl phenoxy)-1H-indenylmethyl-N-methylcarbamate Treat CIS-2,3-dihydro-1-(4-trifluoromethylphenoxy)-N-benzyl-N-methyl-1H-indene-2-methanamine hydrochloride with a sodium hydroxide solution to obtain the oily base CIS-2,3-dihydro-1-(4-trifluoromethylphenoxy)-N-benzyl-N-methyl-1H-indene-2-methanamine. Dissolve CIS-2,3-dihydro-1-(4-trifluoromethylphenoxy)-N-benzyl-N-methyl-1H-indene-2-methanamine (11.9 g, 0.029M) in 150 ml of methylene chloride and to this solution add potassium carbonate (5 g). Add phenylchloroformate (5.4 g, 0.034 M) dropwise and stir the mixture for 3 hours. Sequentially shake the mixture with water, dilute hydrochloric acid and then water. Dry the organic layer over magnesium sulfate. Remove the solvent and recrystallize the residue from cyclohexane to yield 8.9 g (69% yield) of the title compound [melting point=101°–102° C.].
Anal. Calcd. for $C_{25}H_{22}F_3NO_3$: C=68.02; H=5.02; N=3.17. Fd: C=67.88; H=4.94; N=3.36.

Step D:
CIS-2,3-dihydro-N-methyl-1-[4-trifluoromethyl) phenoxy]-1H-inden-2 methanamine hydrochloride Reflux a mixture of phenyl N-[CIS-2,3-dihydro-1-(4trifluoromethyl phenoxy)-1H-indenylmethyl-N-methylcarbamate (4.81 g, 0.01 M), 50 ml of ethanol and 50% sodium hydroxide in water (9.6 g) for 1 hour. Cool the mixture and evaporate the solvent. Take up the residue in ether and water. Separate the ether layer, dry over magnesium sulfate and treat with ethereal hydrogen chloride to yield 1.23 g (34% yield) of the title compound (melting point 192°–193° C.]. Recrystallize the title compound from acetonitrile (melting point 203°–204° C.).
Anal. Calcd. for $C_{18}H_{18}F_3NO.HCl$: C=60.42; H=5.35; N=3.92. Fd: C=60.35; H=5.23; N=4.13.

Step E: (+) and (−)-CIS-2,3-dihydro N methyl-1-[4-trifluoromethyl) phenoxy]-1H inden-2-methanamine hydrochloride Liberate the base of CIS-2,3-dihydro-N-methyl-1-[4-trifluoromethyl) phenoxy]-1H-inden-2-methanamine hydrochloride (4 g) by shaking with ethyl acetate and dilute potassium carbonate solution. Dry the ethyl acetate layer and remove the solvent. To a solution of R-α-methoxyphenylacetic acid (2.05 g) in methylene chloride (60 ml), add thionyl chloride (15 ml) dropwise and reflux the solution for 20 minutes. Remove the solvent and excess thionyl chloride at reduced pressure. Take up the residual acid chloride in methylene chloride (30 ml) and add this solution to a stirred mixture of the above CIS-2,3-dihydro-N-methyl-1-[4-trifluoromethyl) phenoxy]-1H-inden-2-methanamine in 30 ml of methylene chloride, together with 60 ml of 5% sodium hydroxide. After 1 hour, separate the methylene chloride layer, wash with dilute HCl and then with water. Dry the organic layer over sodium sulfate and remove the solvent to leave an oily mixture of diastereomeric amides.

Chromatograph the oil on a 30×7 cm silica gel column in toluene and collect 75 ml fractions. Collect one isomer (isomer A) in fractions 16–21. Collect the other isomer (isomer B) in fractions 27–33. Dissolve each isomer in 250 ml of tetrahydrofuran and add 10 parts by weight of potassium t-butoxide and 0.5 ml of water. Stir for 1 hour and check for the presence of amide by thin layer chromatography. Filter and concentrate the mixtures. Take up the residues in ether and water. Separate the ether layer and wash with saturated sodium chloride solution.

Treatment of the ether solution of isomer A with ethereal HCl yields 0.90 g of the (−)-isomer (melting point =212° C.).

Anal. Calcd. for $C_{18}H_{18}F_3NO \cdot HCl$ (MW 357.80): C=60.42; H=5.35; N=3.92. Fd: C=60.35, 59.85; H=5.31, 5.33; N=3.71, 3.82.

$[\alpha]_D^{20} = -185°$ (C=0.985, MeOH)

Treatment of the ether solution of isomer B with ethereal HCl yields 0.77 g of the (−)-isomer (melting point =217° C.).

Anal. Calcd. for $C_{18}H_{18}F_3NO \cdot HCl$ (MW 357.80): C=60.42; H=5.35; N=3.92. Fd: C=59.93, 59.87; H=5.38, 5.32; N=3.81, 3.81.

$[\alpha]_D^{20} = +183°$ (C=0.958, MeOH)

The starting materials for the above reaction scheme, i.e., the appropriately substituted amino ketones (2) and aryl fluoride/alcohols, are readily obtained through the use of commonly available reagents modified if required through standard synthetic schemes, procedures and techniques as are well known and appreciated by those of ordinary skill in the art.

For example, the appropriate amino alcohol intermediate for compounds of the formula (1) wherein n is 0 can be prepared by procedures analogous to that described by Huebner, et al, [J. Org. Chem. 35, 1149 (1970)].

The appropriate amino ketone starting material for compounds of the formula (1) wherein n is 0, 1 or 2 can be prepared by procedures analogous to that described in U.S. Pat. No. 2,947,756.

In another embodiment, the present invention provides a method of treating depression in a patient in need thereof comprising administering a therapeutically effective antidepressant amount of one or more compounds of the formula (1). In addition, the present invention provides methods of inhibiting synaptic norepinephrine uptake, or of inhibiting synaptic serotonin uptake, or of inhibiting both synaptic norepinephrine and serotonin uptake in a patient in need thereof comprising administering a therapeutically effective inhibitory amount of one or more compounds of the formula (1).

It is generally accepted by those skilled in the art that compounds such as desipramine, which inhibit synaptic norepinephrine uptake, and compounds such as fluoxetine, which inhibit synaptic serotonin (5-hydroxytryptamine or 5-HT) uptake provide antidepresssant effects upon administration to patients suffering from depression.

As used herein, the term "patient" refers to a warm-blooded animal, such as a mammal, which is suffering from depression. It is understood that dogs, cats, rats, mice, horses, bovine cattle, sheep, and humans are examples of animals within the scope of the meaning of the term.

The term "depression" refers to a disease or an abnormal state or condition characterized clinically by a psychiatric syndrome comprising, for example, a dejected mood, psychomotor retardation, insomnia, weight loss, and the like. Depression is readily diagnosed by a clinical diagnostician using practices and procedures well known and appreciated by those of ordinary skill in the art.

It is believed that there is a general correlation between compounds which have a biological effect of inhibiting synaptic norepinephrine or serotonin uptake and the medical effect of being useful in treating depression in a patient suffering therefrom. As used herein, the term "treating depression" refers to providing an antidepressant effect by relieving one or more clinical signs and symptoms of depression in a patient suffering therefrom.

The present invention provides compounds which inhibit both synaptic norepinephrine and serotonin uptake and are therefore believed to be useful in treating depression by administration to a patient suffering therefrom. Although the compounds of the formula (1) inhibit both synaptic norepinephrine and serotonin uptake, in any individual compound these inhibitory effects may be manifested at the same or vastly different concentrations or doses. As a result, some compounds of the formula (1) are useful in treating depression at doses at which synaptic norepinephrine uptake may be substantially inhibited but at which synaptic serotonin uptake is not substantially inhibited. And, conversely, some compounds of the formula (1) are useful in treating depression at doses at which synaptic serotonin uptake may be substantially inhibited but at which synaptic norepinephrine uptake is not substantially inhibited. Other compounds of formula (1) are useful in treating depression at doses at which both synaptic norepinephrine and serotonin uptake are substantially inhibited.

The concentrations or doses at which a test compound inhibits synaptic norepinephrine and serotonin uptake is readily determined by the use of standard assay and techniques well known and appreciated by one of ordinary skill in the art. For example, the degree of inhibition at a particular dose in rats can be determined by the method of Dudley, et al., [J. Pharmacol. Exp. Ther. 217, 834–840 (1981)].

The therapeutically effective inhibitory dose is one which is effective in substantially inhibiting synaptic norepinephrine uptake or synaptic serotonin uptake or both synaptic norepinephrine and serotonin uptake. The therapeutically effective inhibitory dose can be readily determined by those skilled in the art by using conventional range finding techniques and analagous results obtained in the test systems described above. The therapeutically effective inhibitory dose will generally be the same as the therapeutically effective antidepressant dose.

A therapeutically effective antidepressant or inhibitory dose can be readily determined by the attending diagnostician, as one skilled in the art, by the use of conventional techniques and by observing results obtained under analogous circumstances. In determining the therapeutically effective dose, a number of factors are considered by the attending diagnostician, including but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

In treating depression or in inhibiting synaptic norepinephrine and/or serotonin uptake, a compound of formula (1) can be administered in any manner which makes the compound bioavailable in effective amounts, including oral and parenteral routes. For example, compounds of the formula (1) can be administered orally, subcutaneously, intramuscularly, intravenously, transdermally, intranasally, rectally, and the like. Oral administration is generally preferred.

A therapeutically effective antidepressant or inhibitory amount of a compound of the formula (1) is expected to vary from about 0.1 milligrams per kilogram of body weight per day (mg/kg/day) to about 100 mg/kg/day. Preferred amounts are expected to vary from about 1 to about 10 mg/kg/day.

The compounds of this invention can be administered in various forms to achieve the desired effect. The compounds which generally are free amines in liquid form can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may also be formulated and administered in the form of their acid addition salts for purposes of stability, convenience of crystallization, increased solubility and the like where these salts are pharmaceutically acceptable.

In another embodiment, the present invention provides a pharmaceutical composition comprising a therapeutically effective amount of a compound of the formula (1) in admixture or otherwise in association with one or more pharmaceutically acceptable carriers or excipients. The term "therapeutically effective amount" refers to therapeutically effective antidepressant or inhibitory amount as appropriate.

The pharmaceutical compositions are prepared in a manner well known per se in the pharmaceutical art. The carrier or excipient may be solid, semi-solid, or liquid material which can serve as a vehicle or medium for the active ingredient. Suitable carriers or excipients are well known in the art per se. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0-300 milligrams of a compound of the invention.

The tablets, pills, capsules, troches and the like may also contain one or more of the following adjuvants; binders such as microcrystalline cellulose, gum tragacanth or gelatin; excipients such as starch or lactose, disintegrating agents such as alginic acid, Primogel, cornstarch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of the formula (1) in their end-use application.

Compounds of the formula (1) which function as essentially equipotent inhibitors of synaptic norepinephrine and serotonin uptake are generally preferred. Essentially equipotent inhibitors are those which inhibit synaptic norepinephrine and serotonin uptake at substantially the same concentrations or at substantially the same doses (i.e., the therapeutically effective inhibitory dose for synaptic norepinephrine uptake and for synaptic serotonin uptake are substantially equivalent).

Furthermore, compounds of the formula (1) wherein one of $R_1$ and $R_2$ is methyl and the other is hydrogen, and those wherein $R_1$ and $R_2$ are each methyl, are preferred in their end use application. Compounds wherein n is 1 are generally preferred. Compounds wherein p is 0 are also generally preferred. For compounds wherein p is 1, chloro is preferred for Y. Compounds wherein q is 1 are generally preferred. For compounds wherein q is 1, $CF_3$, methoxy and chloro are preferred for X. Finally, the CIS isomeric configuration is the preferred configuration for compounds of the present invention. Furthermore, of those compounds of formula (1) in the CIS isomeric form, the (+) stereoisomeric configuration is generally preferred.

The following compounds are particularly preferred embodiments of the present invention:
2,3-dihydro-1-(2-methoxyphenoxy)-N,N-dimethyl-1H-indene-2-methanamine,
2,3-dihydro-N-methyl-1-[4-(trifluoromethyl)phenoxy]-1H-indene-2-methanamine hydrochloride, and
(+)-CIS-2,3-dihydro-N-methyl-1-[4-(trifluoromethyl)phenoxy]-1H-indene-2-methanamine hydrochloride.

As a further embodiment of the present invention, an improvement is provided in the method of treating depression in a patient in need thereof. This improvement comprises inhibiting both synaptic norepinephrine uptake and synaptic serotonin uptake in the depressed patient. This improved treatment can be effected by administering a therapeutically effective inhibitory amount of a compound which functions as both a synaptic norepinephrine and serotonin uptake inhibitor or by conjunctive therapy with therapeutically effective inhibitory amounts of (a) a compound which functions as a synaptic norepinephrine uptake inhibitor, and (b) a compound which functions as a synaptic serotonin uptake inhibitor.

As indicated above, it is generally believed that there is a correlation between compounds which have a biological effect of inhibiting synaptic norepinephrine uptake such as desipramine, or synaptic serotonin uptake, such as fluoxetine, and the medical effect of being useful in treating depression in a patient suffering therefrom. This inhibition of norepinephrine or serotonin uptake in the synaptic gap is believed to effect a down-regulation of $\beta$-adrenergic receptors which correlates well with the onset of clinical effectiveness of compounds which are useful in treating depression. Surprisingly, applicants now have found that inhibition of both synaptic norepinephrine and serotonin uptake in a patient suffering from depression has a synergistic beneficial effect in effecting a down-regulation of $\beta$-adrenergic receptors and therefore believe that this treatment will provide a significant improvement in the treatment of depression.

The number of $\beta$-adrenergic receptors in rat cerebral cortical membranes was measured after a 4 day and 14 day course of one of the following treatments:
a) saline control (intraperitoneal injection—i.p.)
b) desipramine (5 mg/kg/day, i.p.)
c) fluoxetine (10 mg/kg/day, i.p.) or (10 mg/kg bid, i.p.)
d) desipramine (5 mg/kg/day, i.p.) and fluoxetine (10mg/kg/day, i.p.) or (10 mg/kg bid, i.p.)

Male Sprague-Dawley rats (175-200 g) were assigned randomly to one of the four treatment groups above and were treated as indicated for either 4 or 14 days. The animals were sacrificed 24 hours after their last treatment and cerebral cortical membranes were isolated. These membranes were assayed for $\beta$-adrenergic receptor number by the method of Bylund and Snyder [Mol. Pharmacol. 12, 568 (1976)] by measuring the amount of [3H]dihydro-alprenolol ($[^3H]$-DHA) bound. The results as shown in Table 1 indicate that combined treatment with desipramine and fluoxetine results in a substantially greater down-regulation of $\beta$-adrenergic receptors than treatment with either desipramine or fluoxetine alone. Furthermore, the combined treatment results in a synergistic effect in providing a down-regulation which is substantially greater than what would have been expected if desipramine and fluoxetine produced merely additive effects on $\beta$-adrenergic receptor down-regulation.

TABLE 1

The Effect of the Combined Treatment with Desipramine and Fluoxetine on Rat Cortical $\beta$-Receptors

| Treatment | $[^3H]$-DHA Specifically Bound (fmol/mg protein) | % Control |
|---|---|---|
| A) Saline | 41.8 ± 1.4 | — |
| Desipramine | 35.9 ± 1.2* | 86 |
| Fluoxetine | 37.9 ± 1.8 | 91 |
| Desipramine + Fluoxetine | 26.5 ± 1.2*+ | 64 |
| B) Saline | 54.6 ± 3.1 | — |
| Desipramine | 49.2 ± 2.4 | 90 |
| Fluoxetine | 51.8 ± 1.7 | 95 |
| Desipramine + Fluoxetine | 40.0 ± 0.9* | 73 |

A) Desipramine (5 mg/kg, i.p.) and Fluoxetine (10 mg/kg, i.p.) were administered as indicated for 14 days. Six animals per group. Values are mean ± SEM.
B) Desipramine (5 mg/kg, i.p.) and Fluoxetine (10 mg/kg bid, i.p.) were administered as indicated for 4 days. Six animals per group. Values are mean ± SEM.
*p < 0.05 vs saline
+P < 0.05 vs Desipramine Compounds which function as synaptic norepinephrine uptake inhibitors and/or synaptic serotonin uptake inhibitors are readily identified by standard techniques and procedures well known and appreciated by those skilled in the art, such as, for example, the method described by Dudley, et al. [J. Pharmacol. Exp. Ther. 217, 834 (1981)]. Therapeutically effective inhibitory amounts of these compounds can be determined as described above. As used herein, the term "conjunctive therapy" refers to coadministration of a compound which functions as synaptic norepinephrine uptake inhibitor along with a compound which functions as a synaptic serotonin uptake inhibitor at essentially the same time.

The following are examples of synaptic serotonin uptake inhibitors which can be used according to the present invention in conjunctive therapy with a synaptic norepinephrine uptake inhibitor: fluoxetine, citalopram, zimelidine, paroxetine, and the like. The following are examples of synaptic norepinephrine uptake inhibitors which can be used according to the present invention in conjunctive therapy with a synaptic serotonin uptake inhibitor: desipramine, nortriptyline and the like.

Of course, certain compounds, such as those of the present invention, function as both synaptic norepinephrine uptake inhibitors and synaptic serotonin uptake inhibitors. Administration of such compounds which function as inhibitors of synaptic norepinephrine and serotonin uptake is also understood to be within the scope of the present invention. Administration of compounds which function as essentially equipotent inhibitors of synaptic norepinephrine and serotonin uptake is preferred.

In effecting this improvement in the treatment of depression, one or more compounds which function as synaptic norepinephrine and synaptic serotonin uptake inhibitors may be administered to a patient in the same manner as described above for the compounds of this invention.

What is claimed is:

1. A compound of the formula

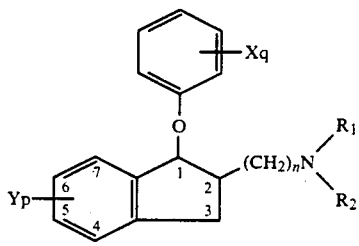

wherein
p and q are each independently 0, 1 or 2,
n is 1,
Y and X are each independently lower alkyl, lower alkoxy, hydroxy, $CF_3$, or halogeno,
$R_1$ and $R_2$ are each independently hydrogen, lower alkyl, or aralkyl,
or an acid addition salt thereof.

2. A compound of claim 1 wherein one of $R_1$ and $R_2$ is methyl and the other is hydrogen.

3. A compound of claim 1 wherein $R_1$ and $R_2$ are each methyl.

4. A compound of claim 1 wherein p is O.

5. A compound of claim 1 wherein Y is fluoro and p is 1.

6. A compound of claim 1 wherein X is $CF_3$ and q is 1.

7. A compound of claim 1 wherein X is methoxy and q is 1.

8. A compound of claim 1 wherein q is O.

9. A compound of claim 1 wherein X is chloro and q is 1.

10. A method of treating depression in a patient in need thereof comprising administering a therapeutically effective antidepressant amount of one or more compounds of claim 1.

11. A method of inhibiting norepinephrine uptake in a patient in need thereof comprising administering a therapeutically effective inhibitory amount of one or more compounds of claim 1.

12. A method of inhibiting serotonin uptake in a patient in need thereof comprising administering a therapeutically effective inhibitory amount of one or more compounds of claim 1.

13. A compound of claim 1 wherein the compound is 2,3-dihydro-1-(2-methoxyphenoxy)-N,N-dimethyl-1H-indene-2-methanamine.

14. A compound of claim 1 wherein the compound is 2,3-dihydro-N-methyl-2-[4-(trifluoromethyl)-phenoxy]-1H-idene-2-methanamine hydrochloride.

15. A compound of claim 13 wherein the compound is CIS-2,3-dihydro-1-(2-methoxyphenoxy)-N,N-dimethyl-1H-indene-2-methanamine.

16. A compound of claim 14 wherein the compound is CIS-2,3-dihydro-N-methyl-2-[4-(trifluoromethyl)-phenoxy]-1H-indene-2-methanamine hydrochloride.

17. A compound of claim 13 wherein the compound is (+)-CIS-2,3-dihydro-1-(2-methoxyphenoxy)-N,N-dimethyl-1H-idene-2-methanamine.

18. A compound of claim 14 wherein the compound is (+)-CIS-2,3-dihydro-N-methyl-2-[4-(trifluoromethyl)-phenoxy]-1H-indene-2-methanamine hydrochloride.

* * * * *

UNITED STATES PATENT AND TRADEMARK OFFICE
CERTIFICATE OF CORRECTION

PATENT NO. : 5,149,714
DATED : September 22, 1992
INVENTOR(S) : Jules Freedman

It is certified that error appears in the above-identified patent and that said Letters Patent is hereby corrected as shown below:

Column 1, Line 7 the patent reads: "This a", and should read --This is a--.

Column 1, line 36 the patent reads: "qhen", and should read --when--.

Column 3, line 38 the patent reads: "available form", and should read --available from--.

Column 6, line 31 the patent reads: "-1phenoxy", and should read -- -1-phenoxy--.

Column 6, line 46 the patent reads: "$C_{21}H_{25}NOhd 3.C_2H_2O_4$:", and should read --$C_{21}H_{25}NO_3 \cdot C_2H_2O_4$--.

Column 8, line 56 the patent reads: "(4trifluoromethyl", and should read --(4-trifluoromethyl--.

UNITED STATES PATENT AND TRADEMARK OFFICE
CERTIFICATE OF CORRECTION

PATENT NO. : 5,149,714
DATED : September 22, 1992
INVENTOR(S) : Jules Freedman

It is certified that error appears in the above-identified patent and that said Letters Patent is hereby corrected as shown below:

```
Column 16, line 31 the patent reads: "methyl-2", and
should read --methyl-1--.

Column 16, line 37 the patent reads: "methyl-2", and
should read --methyl-1--.

Column 16, line 43 the patent reads: "methyl-2", and
should read --methyl-1--.
```

Signed and Sealed this

Twenty-seventh Day of September, 1994

Attest:

BRUCE LEHMAN

*Attesting Officer*   *Commissioner of Patents and Trademarks*